US00PP12376P2

(12) United States Plant Patent
Snow

(10) Patent No.: US PP12,376 P2
(45) Date of Patent: Jan. 29, 2002

(54) BEGONIA PLANT NAMED '77VR ROSE RED'

(75) Inventor: Andrew B. Snow, Aptos, CA (US)

(73) Assignee: Golden State Bulb Growers, Moss Landing, CA (US)

( * ) Notice: Subject to any disclaimer, the term of this patent is extended or adjusted under 35 U.S.C. 154(b) by 0 days.

(21) Appl. No.: 09/488,411

(22) Filed: Jan. 21, 2000

(51) Int. Cl.[7] ..... A01H 5/00
(52) U.S. Cl. ..... Plt./349
(58) Field of Search ..... Plt./349

*Primary Examiner*—Bruce R. Campell
*Assistant Examiner*—Susan B. McCormick
(74) *Attorney, Agent, or Firm*—Foley & Lardner

(57) ABSTRACT

A new and distinct cultivar of Begonia plant named '77VR Rose Red' characterized by having a definite and distinct flower fragrance that can be described as sweet and lingering but subtle and not overpowering. It is often compared to the scent of a fragrant rose bloom. The fragrance is most pronounced when the temperature is between 65° and 80° F. Male flowers are fully double and do not produce pollen or male reproductive parts under normal growing conditions. The cultivar '77VR Rose Red' has a full and semi-pendulous plant habit with numerous flower shoots (4–6 or more). Each flowering shoot will produce anywhere from 4–6 peduncles with 1 or 2 male flowers on each during the growing season.

2 Drawing Sheets

BACKGROUND OF THE INVENTION

The present invention relates to a new and distinctive cultivar of Begonia plant, botanically known as *Begonia tuberhybrida* (Pendula-type), and known by the cultivar name '77VR Rose Red'.

The new cultivar is a product of a planned breeding program and was originated from a hybridization made during such a program in Watsonville, Calif. in 1994. The female or seed parent was a proprietary Begonia selection designated 77MR-4057 (unpatented). The male or pollen parent was a proprietary Begonia selection designated 77MK-4056 (unpatented). '77VR Rose Red' was discovered and selected within the progeny of the stated cross by the inventor, Andrew B. Snow, in a controlled environment in Watsonville, Calif. in 1995.

The first act of asexual reproduction of '77VR Rose Red' was accomplished by leaf and stem cuttings in 1996 in a controlled environment in Moss Landing, Calif. by Andrew B. Snow. Horticultural examination of selected units has demonstrated that the combination of characteristics as herein disclosed for '77VR Rose Red' are firmly fixed and are retained through successive generations of asexual reproduction.

BRIEF DESCRIPTION OF THE INVENTION

The following characteristics distinguish the new cultivar from both its parents and other Begonia cultivars commercially known and used in the floriculture industry:

1. a definite and distinct flower fragrance that can be described as sweet and lingering but subtle and not overpowering . It is often compared to the scent of a fragrant rose bloom. The fragrance is most pronounced when the temperature is between 65° and 80° F.;

2. male flowers which are fully double and do not produce pollen or male reproductive parts under normal growing conditions; and 3. full and semi-pendulous plant habit with numerous flower shoots (4–6 or more). Each flowering shoot will produce anywhere from 4–6 peduncles with 1 or 2 male flowers on each during the growing season.

'77VR Rose Red' has not been observed under all possible environmental conditions. The phenotype of the new cultivar may vary significantly with variations in environment such as temperature, light intensity, and daylenth without any change in genotype.

Of the many commercial cultivars known to the present inventor, there is no known Begonia cultivar with which the new cultivar can be meaningfully compared. The color variance and gradation is unique, as is the distinct fragrance.

BRIEF DESCRIPTION OF THE DRAWINGS

The accompanying color photographic illustrations were taken on Aug. 20, 1999, and show typical flower and foliage characteristics of '77VR Rose Red' when grown in a 10-inch plastic pot, with colors being as true as possible with illustrations of this type.

Sheet 1 is a side elevational view of '77VR Rose Red'.

Sheet 2 is a top view of the claimed cultivar showing the characteristics of the upper and lower surfaces of the flower and foliage.

DETAILED BOTANICAL DESCRIPTION

The following observations, measurements, and values describe a 2 year old tuber of '77VR Rose Red' as grown in Watsonville, Calif. under conditions which approximate those generally used in commercial practice. The plant is grown in a greenhouse with ambient temperatures of 60–75° F. The greenhouse is provided with a 50% shade cover that limits the light to under 2000 foot-candles. '77VR Rose Red' is grown in a soiless mix and fed with a regular, complete fertilizer such as 20-10 -20 at a rate of 200 ppm N, once every week.

Color references are made to The Royal Horticultural Society (R.H.S.) Colour Chart exept where general terms of ordinary dictionary significance are used.

Classification:

*Botanical.*—A hybrid of the genus *Begonia tuberhybrida* (Pendula-type).

*Commercial.*—Begonia cv. 77VR Rose Red.

Parentage:

*Male parent.*—Begonia cultivar designated 77MK-4056.

*Female parent.*—Begonia cultivar designated 77MR-4057.

Propagation:

*Type cutting.*—Leaf and stem cuttings.

*Time to root.*—Approximately 24 to 30 days at 21° C. (summer) and 32 to 38 days at 21° C. (winter).

*Rooting habit.*—Abundant, fibrous and dendritic.

*Time for shoot development.*—Slow, 10 to 14 weeks in summer and up to 16 weeks in winter.

Plant:

*Form.*—Low mounding, semi-pendulous and herbaceous.

*Growth habit.*—Slow, uniform growth with numerous shoots and moderate branching habit at full growth. The plant is well rounded with a height of about 10 to 15 inches, excluding the container, with up to 20 -inch pendulous shoots. The width is approximately 24 inches.

Foliage:

*Habit.*—Simple, alternate, and borne on semi-rigid petioles 3 to 6 inches in length.

*Size.*—At maturity, the leaves reach 7 to 9 inches from base to apex, and at their widest point the leaves are 5 to 6 inches in width.

*Shape.*—Triangular-cordate with acuminate tip between rounded-based lobes.

*Texture.*—Firm, crisp, but not brittle; sparsely hirtellous on both surfaces.

*Margin.*—Doubly serrate.

*Color.*—Immature: Top surface: RHS 137 A with red cast. Under surface: RHS 46B with RHS 142B near the veins. Mature: Top surface: RHS 147A. Under surface: RHS 138B with a cast of red, RHS 47B, between the veins.

*Venation.*—Reticulate.

*Vein color.*—RHS 146D.

Flower:

*Habit.*—Flowering is presented on a pendulous raceme. Often, but not always, secondary male and female flowers will develop below the primary male and female flowers. Some peduncles have a solitary male flower, while others may have a solitary male flower accompanied by either a solitary secondary male flower or matching female flower and occasionally a secondary male and female flower.

*Natural flowering season.*—Summer and fall months.

*Size.*—Male: Approximately 3.5 to 5 inches. Female: Approximately 2.5 to 3.5 inches.

*Buds.*—Flat, nearly round, tending towards bell shaped. RHS 46B, a consistent measurement is not possible due to the continuous development and swelling of the bud.

*Borne.*—On small pedicles originating from long (5 to 8 inches) axillary peduncles, resulting in a solitary male flower, a solitary male and one or two female flowers, and occasionally secondary male and female flowers as raceme develops.

*Pedicel.*—Length: 4 to 5 cm, Diameter: 3 to 4 mm, Color: RHS 45A, where exposed to direct light. RHS 153 D with cast of RHS 26C, where it gets indirect light.

*Quantity.*—Approximately 2 to 5 flowers per peduncle and numerous (3 to 5 ) peduncles per shoot, with 5 to 7 shoots per plant.

Tepals:

*Shape.*—Obovate.

*Color.*—Top surface: In spring and summer when opening, RHS 46C. Under surface: RHS 46C or slightly darker.

*Number.*—Approximately 50 to 60 on male flowers and 5 on female flowers.

*Size.*—Outer (male) from 2×1 inches to 2.25×1.5 inches (length×width).

*Texture.*—Smooth.

Reproductive organs:

*Stamens.*—Petaloid. Male produces approximately 50–60, female 5.

*Pistils.*—1, compound with 3 chambers. Stigma: Multilobed, RHS 17A. Style: Short, RHS 17A. Ovaries: Number: 3. Size: Approximately ½–¾ inches. Color: RHS 144C with RHS 46A–B on tips if grown in high light.

Resistance to Disease: Good. No seed or fruit production has been observed to date.

I claim:

1. A new and distinct cultivar of Begonia plant named '77VR Rose Red', as illustrated and described.

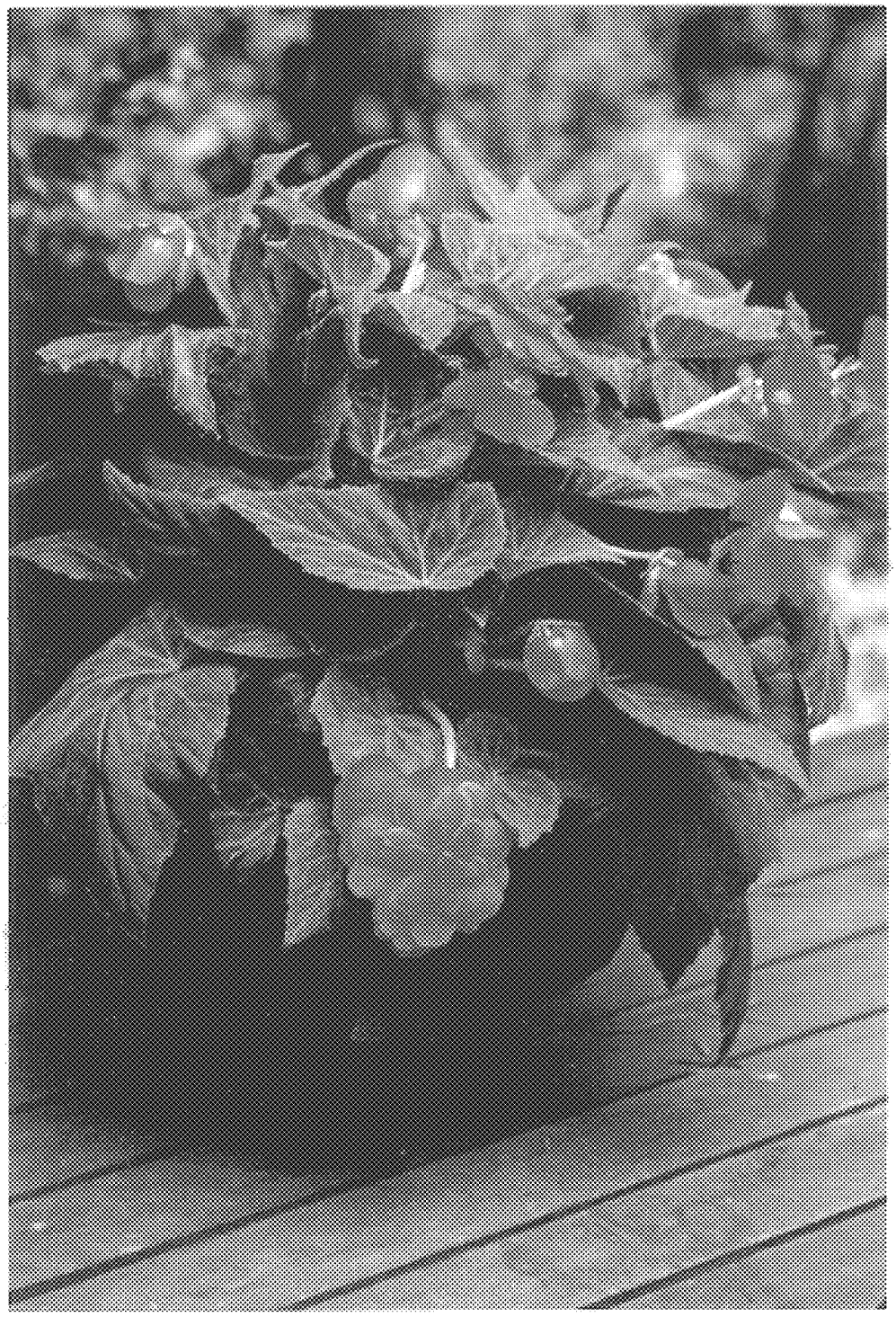

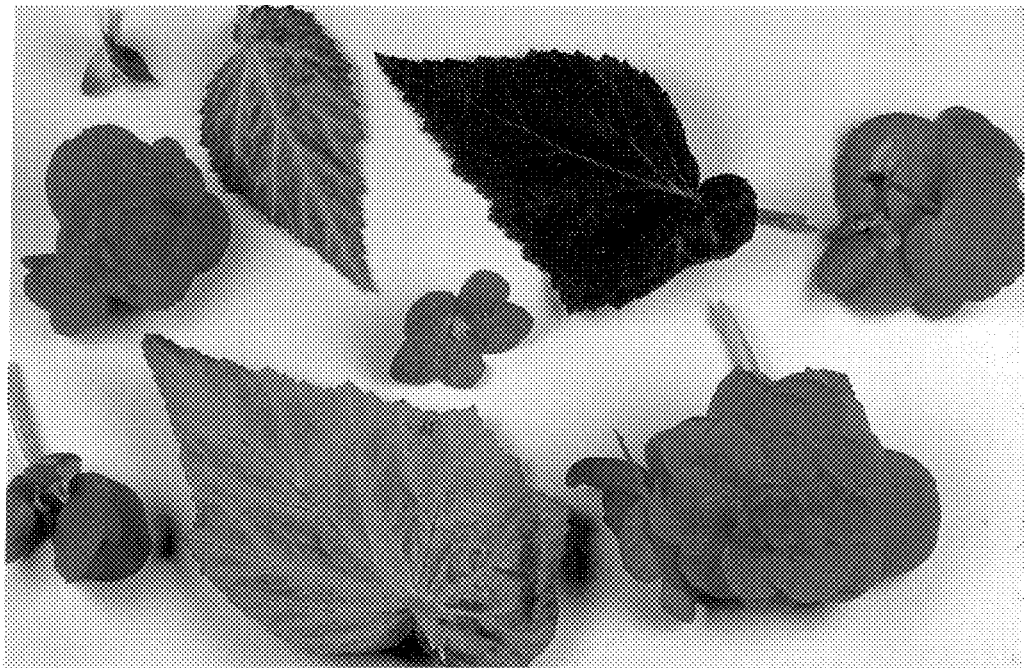

* * * * *